United States Patent [19]

Meehan

[11] Patent Number: 5,728,052
[45] Date of Patent: Mar. 17, 1998

[54] WATERPROOF ENCLOSURE

[76] Inventor: John J. Meehan, 16 Robin Rd., Rye, New Hampshire, N.H. 03870

[21] Appl. No.: 717,422

[22] Filed: Sep. 20, 1996

[51] Int. Cl.⁶ ............................. A61F 5/00; A61F 13/00
[52] U.S. Cl. ............................................ 602/3; 602/60
[58] Field of Search ............................. 602/3, 13, 14, 602/23, 60–66

[56] References Cited

U.S. PATENT DOCUMENTS

| | | | |
|---|---|---|---|
| 3,785,374 | 1/1974 | Lipson | 128/82 |
| 4,098,268 | 7/1978 | Scott | 128/82 |
| 4,135,503 | 1/1979 | Romano | 602/13 |
| 4,139,003 | 2/1979 | Little et al. | 128/82 |
| 4,346,699 | 8/1982 | Little et al. | 128/82 |
| 4,387,710 | 6/1983 | Beatty, III | 128/91 R |
| 4,562,834 | 1/1986 | Bates | 602/3 |
| 4,768,501 | 9/1988 | George | 128/82 |
| 4,822,371 | 4/1989 | Jolly | 623/32 |
| 4,966,135 | 10/1990 | Renfrew | 602/3 |
| 5,394,624 | 3/1995 | Siepser | 36/9 R |
| 5,593,453 | 1/1997 | Ahlert | 602/3 |

FOREIGN PATENT DOCUMENTS

| | | | |
|---|---|---|---|
| 630633 | 12/1994 | European Pat. Off. | 602/23 |
| 3011724 | 10/1981 | Germany. | |
| 93014730 | 8/1993 | WIPO | 602/60 |

*Primary Examiner*—Richard J. Apley
*Assistant Examiner*—Denise Pothier
*Attorney, Agent, or Firm*—Nutter, McClennen & Fish, LLP

[57] ABSTRACT

A waterproof enclosure includes a pliable, waterproof, elongated sheath having either a closed end and an open end, or two open ends; and a resilient, waterproof, sealing element associated with each open end. A pliable, waterproof, bellows can be interposed between and contiguous with the end of each sealing element and the sheath. Each sealing element may include a first end that is of smaller diameter than a second end, a frustroconical shape, and ribs. A closed sheath end may have a rough surface to improve traction. A gas passage through the sheath can be provided that includes a port actuatable from a first state for inhibiting gas movement through the gas passage and a second state for permitting gas movement through the gas passage. The port can be manually movable from the first state to the second state, and it can include a pressure relief valve. The waterproof enclosure can include a loop integral with the exterior surface of the sheath to which an elasticized cord may be attached. An apertured covering that encloses at least a portion of the waterproof enclosure is also disclosed.

15 Claims, 4 Drawing Sheets

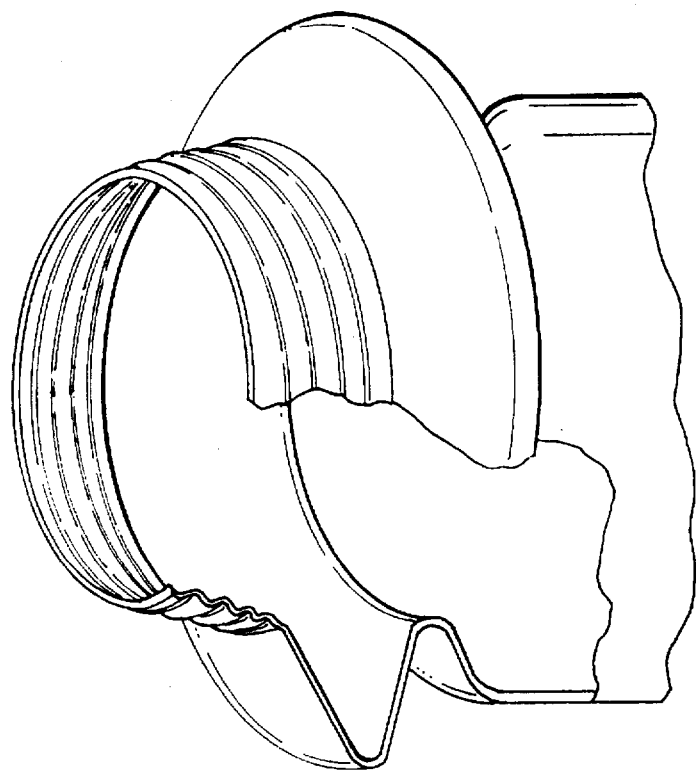
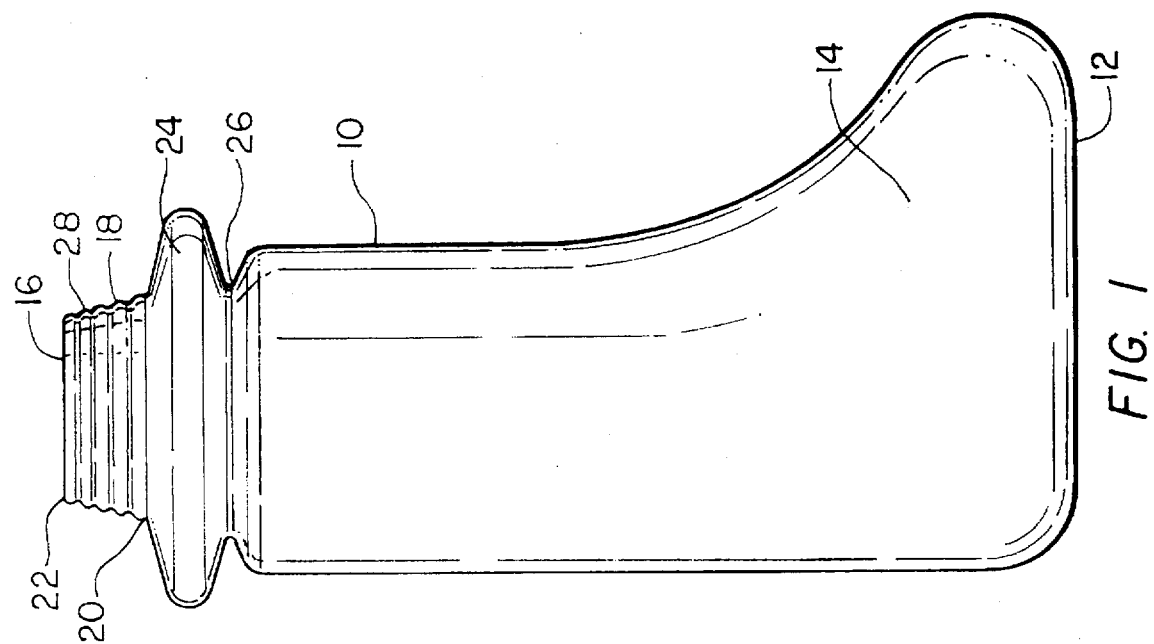

WATERPROOF ENCLOSURE

FIELD OF THE INVENTION

The invention relates to a waterproof enclosure, and more particularly to a waterproof cover for a human limb.

BACKGROUND OF THE INVENTION

Plaster of Paris is calcined gypsum, which when mixed with water, forms a thick paste that sets quickly and is commonly used for medical casts among other applications. Once dry however, a plaster cast is very vulnerable to water damage. If moistened, a plaster cast softens; and if submersed in a liquid, a plaster cast disintegrates. Thus, a cast wearer is obliged to make lifestyle changes to keep the cast as dry as possible for a several month period of bone mending. Examples of lifestyle changes may include the substitution of baths for showers and discontinuance of swimming. Although waterproof fiberglass casts are known, plaster casts remain ubiquitous.

In recognition of the vulnerability of plaster casts, attempts have been made to fashion waterproof coverings for a cast. For example, it is not unknown for individuals to place a plastic bag loosely over a cast while showering. Of course such a makeshift solution is not satisfactory with respect to protection, comfort, or convenience. An attempt to improve on the plastic bag is disclosed in U.S. Pat. No. 4,139,003 wherein a very large condom is rolled over a hand and cast covered arm. U.S. Pat. No. 4,346,699 discloses a loose bag with an elastic aperture. German patent document DE 3011-724 discloses a sleeve that has an inflatable cuff proximate an aperture in the sleeve; and U.S. Pat. No. 4,098,268 includes a cuff that is secured with a hook and pile fastener. Even if these devices provide protection in a non-immersion situation such as taking a shower, they are particularly deficient in total immersion situations such as encountered during hydrotherapy, swimming or scuba diving.

When a limb or other body portion is enclosed along with air in a bag, and the bag covered body portion is submerged in water, the gas forms a "bubble" that seeks an escape path, such as the intersection of the aperture of the bag and the body. When the bubble is liberated from the bag, water is allowed to enter the bag. In addition, if air does not escape from the bag, the bag can be very buoyant, annoying, and a swimming impediment. The larger the bubble, the greater the annoyance. None of the above-identified patents recognize or address these problems.

By contrast with the loose gas-filled bags described above, U.S. Pat. No. 4,768,501 discloses a method for waterproof sealing of casts and dressings that is closely akin to vacuum packing food with plastic wrap. Specifically, the '501 patent teaches a method of covering a limb and cast with a very thin membrane and aspirating air from the membrane with a pump to achieve a vacuum seal to the extent that such is possible. Even if this technique were to be effective in protecting a submerged cast, it appears to be very cumbersome, tedious, and expensive. Additionally, even though the membrane is identified as being flexible latex, there does not appear to be any sealing element other than the overall vacuum seal. Furthermore, obtaining and maintaining a vacuum tight seal on human skin is much more challenging than wrapping a styrofoam container with plastic wrap. It is difficult to imagine that the disclosed vacuum sealed membrane would remain sealed around the moving, flexing limb of a swimmer.

Yet another problem with the known cast covers is their unsuitability for protecting a cast or other dressing on an intermediate portion of a limb or on the abdomen when it may be desired to not encase the lower portion of the limb or body. Specifically, the known covers do not provide a second opening in the cover.

SUMMARY OF THE INVENTION

The present invention overcomes the disadvantages of the known waterproof covers by providing a waterproof enclosure with an improved seal that is secure and capable of maintaining a fluid tight seal on a moving limb or body. In an exemplary embodiment, a waterproof enclosure includes a pliable, waterproof, elongated sheath having at least one open first end and a resilient, waterproof, sealing element contiguous with the open first end of the sheath.

The waterproof enclosure can further include an open second end with a contiguous sealing element. If the second end of the waterproof enclosure is closed, it may include a rough surface to improve traction.

A pliable, waterproof, bellows can be interposed between and contiguous with the first and/or second end of the sheath and a respective sealing element(s).

The sealing element(s) may include a first end having a smaller diameter than a second sheath end, a frustroconical shape, and ribs.

In another embodiment of the invention, the waterproof enclosure includes a gas passage through the sheath. The gas passage may include a port that is actuatable from a first state for inhibiting gas movement through the gas passage and a second state for permitting gas movement through the gas passage. The port can be manually movable from the first state to the second state, and it can include a pressure relief valve.

In yet another embodiment of the invention, the waterproof enclosure includes one or more loops integral with the exterior surface of the sheath to which one or more elasticized cords may be attached.

Each of the embodiments of the waterproof cover can include an apertured covering that encloses at least a portion of the waterproof enclosure.

BRIEF DESCRIPTION OF THE DRAWINGS

A more complete understanding of the present invention and the attendant advantages and features thereof will be more readily understood by reference to the following detailed description when it is considered in conjunction with the accompanying drawings wherein:

FIG. 1 is a plan view of a waterproof enclosure according to the present invention;

FIG. 1A is a perspective view of sealing element illustrated in FIG. 1 that has been sectioned to reveal the interior surface of the sealing element;

DETAILED DESCRIPTION OF THE INVENTION

Figure 2:
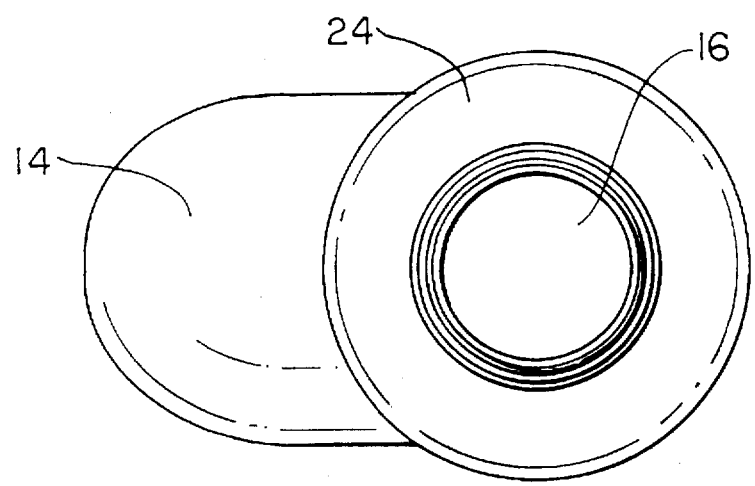
FIG. 2 is a top view of the waterproof enclosure of FIG. 1.

FIG. 1 illustrates a waterproof enclosure including a pliable, waterproof, elongated sheath 10 that is dimensioned to receive a human limb encased in a cast or other dressing. Although the sheath 10 can be a "skin tight" elastic material, for comfort and ease of donning and doffing the waterproof enclosure is large enough to be characterized as at least somewhat loose fitting. A closed distal end 12 of the sheath 10 can include an enlarged or easily expandable area 14 to accommodate and allow movement of a hand or foot. The sheath 10 can be fabricated from a variety of waterproof materials, including natural or synthetic rubbers, polymers, elastomers, or latexes. The interior of the sheath 10 can include a lining to improve comfort for the wearer.

The illustrated embodiment is configured to receive a cast-covered lower leg through an open end 16 that is defined by a resilient, waterproof, sealing element 18 having a distal end 20 and a proximal end 22. A pliable, waterproof bellows 24 is interposed between and contiguous with the distal end 20 of the sealing element 18 and the proximal end 26 of the sheath 10. The bellows 24 are to be understood as a very flexible region of the waterproof enclosure that allows the sealing element 18 to easily articulate with respect to the sheath 10 and/or be easily moved toward or away from the proximal end 26 of the sheath. FIG. 1 illustrates the bellows 24 as a single roll or increased amount of waterproof fabric. However, multiple folds or curves, or a folded accordion-like configuration is acceptable. The bellows 24 between the sealing element 18 and the sheath 10 allows for movement of the limb without pulling on, stressing, or damaging the sealing element. Although the sealing element 18, bellows 24, and sheath 10 are described as discrete elements, it should be understood that they can be formed as a single unitary element or joined in a fluid tight manner using fabrication techniques known to those skilled in the art.

The sealing element 18 can have a substantially cylindrical or annular configuration or, as shown in FIG. 1, the sealing element can have a proximal end 22 that is smaller in diameter than the distal end 20. Further, as shown, the sealing element 18 can have a tapered or frustroconical shape. In the illustrated embodiment, the sealing element 18 is 2 to 4 inches in length, but may be shorter or longer as desired. Flexibility, comfort, and sealing performance can be further enhanced by providing ribs 28 that bulge from the interior face of the sealing element 18 as shown in FIG. 1A. The ribs 28 can extend beyond the surface of the sealing element in a range of less than 1 mm to 1 cm. Each of several ribs may extend a different distance from the surface of the sealing element and be unevenly spaced apart. Alternatively, ribs 28 can bulge from the exterior surface of the sealing element, in lieu of or in addition to the interior bulging ribs. In embodiments with two sealing elements, the sealing elements can be configured differently. Furthermore, although the sheath 10 is illustrated with a bellows 24, interposed between the sheath and the sealing element 18, other embodiments of the sheath omit the bellows and include a sealing element directly attached to the sheath.

FIG. 2 is a view of the waterproof enclosure viewed from the top. The open end 16 into which the limb is inserted is shown to be noticeably smaller in diameter than the adjacent bellows 24. The enlarged portion 14 of the sheath 10 is also visible.

Figure 3:
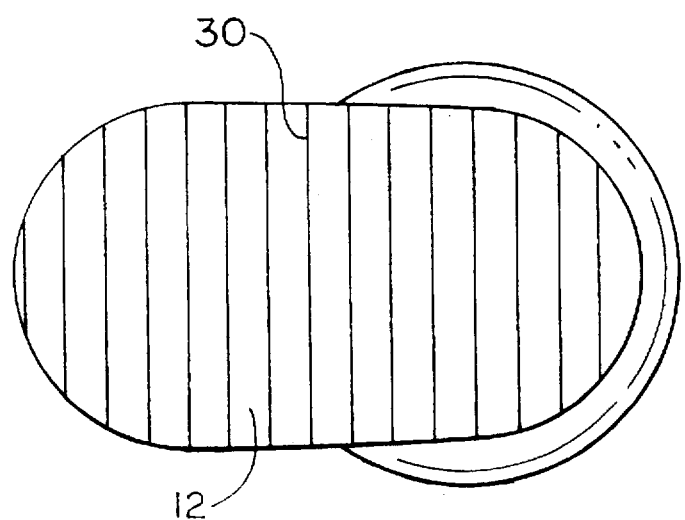
FIG. 3 is a bottom view of the waterproof enclosures of FIG. 1.

FIG. 3 illustrates the bottom or distal end 12 of the sheath 10 of the waterproof enclosure. In this embodiment, the distal end 12 is rough to increase friction or to improve traction. However, additional portions of the sheath 10 can include a rough surface as required. The rough surface can include integral surface relief features such as bumps or ridges 30, a textured cover layer, or a sprayed-on material known to those skilled in the art to reduce slippage or to provide aesthetic features.

Figure 4:
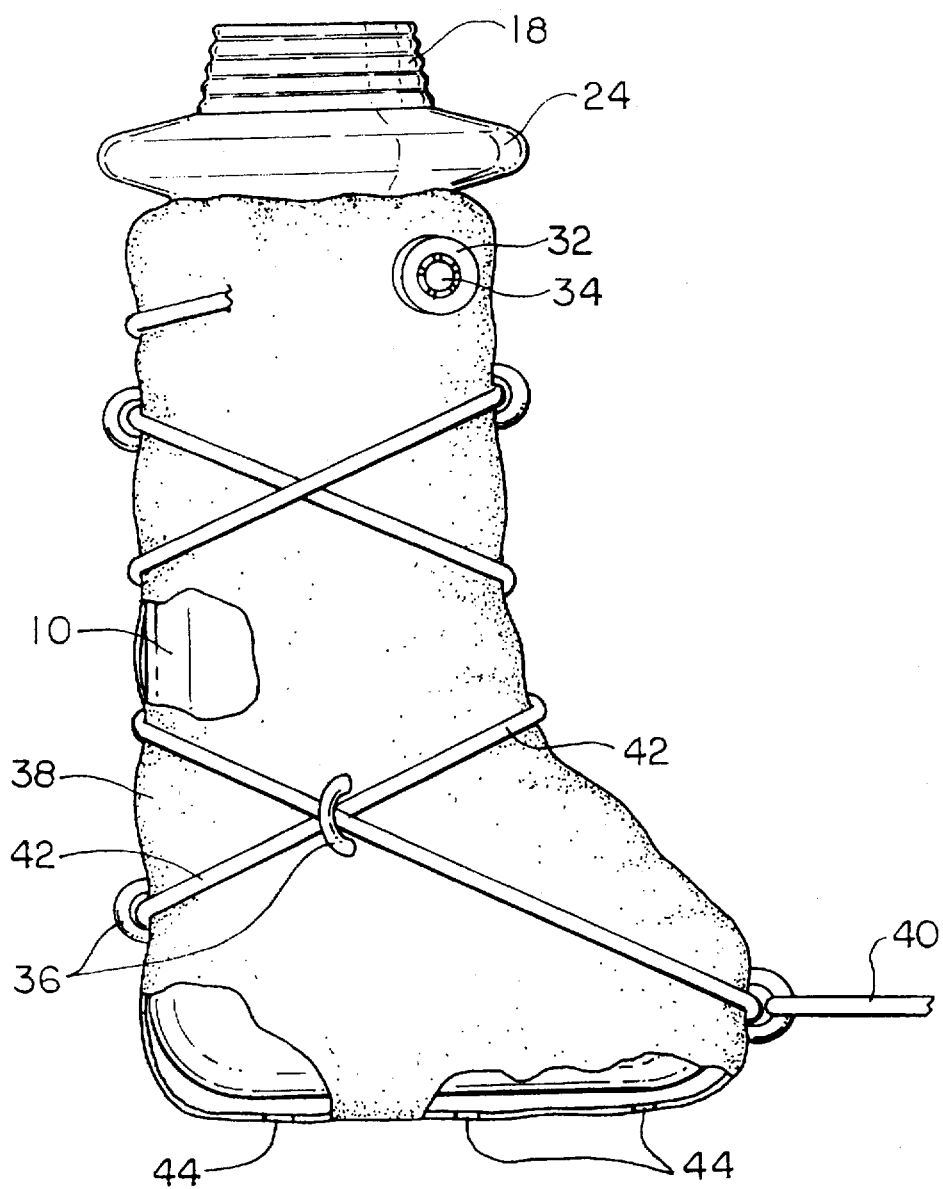
FIG. 4 is an alternative embodiment of the waterproof enclosure that includes a pressure relief valve.

Referring to FIG. 4, an embodiment of the waterproof enclosure is illustrated that provides several additional features that render the invention particularly well suited for complete submersion situations such as swimming. In addition to the features and benefits described hereinabove, the waterproof enclosure of FIG. 4 includes a gas passage 32 through the sheath 10. The gas passage 32, such as a tube, can include a port 34 that is actuatable from a first state for inhibiting gas movement through the gas passage and a second state for permitting gas movement through the gas passage. Examples of a port 34 include a screw valve, a biased valve, or other fluid control valves known to those skilled in the art, that are manually movable from the first state to the second state.

In addition to, or instead of, a manually operable opening and closing element, the port 34 can consist of or include a pressure relief valve that permits gas to pass from the interior of the sheath to the exterior of the sheath when the gas pressure within the sheath exceeds a predetermined pressure. The provision of a gas passage, port, and/or pressure relief valve is particularly important with respect to complete immersion activities to relieve stress from the sealing element. Although the pressure relief valve is positioned adjacent to the bellows in the illustrated embodiment, it could be placed almost anywhere on the sheath or even the bellows.

Continuing to refer to FIG. 4, the waterproof enclosure is provided with one or more loops 36 that are integral with the exterior surface of the sheath or integral with a cover 38 that encloses the sheath 10. One or more elasticized cords 40 can be attached to the one or more loops 36 at a first cord end and tethered to the side of a swimming pool at the other cord end. This enables a user to exercise an injured limb in a weightless environment through tethered swimming or resistance movements. The loops 36 can also serve as guides for strapping 42 that firmly secures the cover 38 to the sheath 10 and distributes forces across the sheath. In addition to providing loops 36 for attachment to elasticized cords 40, the cover 38 protects the sheath 10 from puncture and can be configured as desired for ornamental purposes. In an exemplary embodiment, the cover 38 is made of a fabric and is provided with one or more apertures 44 to allow the cover to drain and to dry after use.

Figure 5:
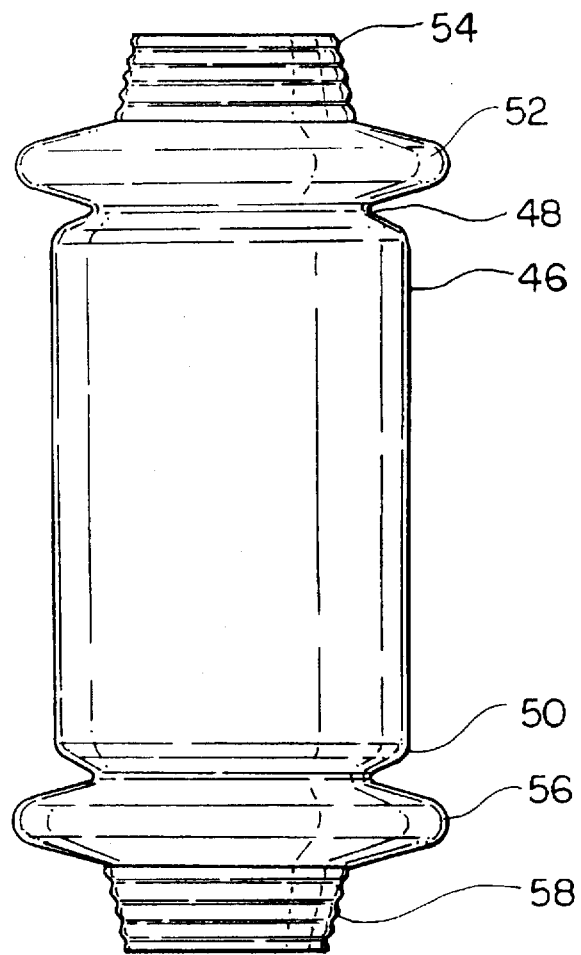
FIG. 5 illustrates still another embodiment of the waterproof enclosure.

Referring now to FIG. 5, another embodiment of the waterproof sheath is illustrated that includes a pliable, waterproof, elongated sheath 46 that is dimensioned to receive a human limb, chest, or abdomen. The sheath 46 is open at both a first end 48 and a second end 50. As with other embodiments of the sheath, the sheath 46 can be fabricated from a variety of waterproof materials and the interior of the sheath can be lined to improve comfort. The sheath can further include a first bellows 52 interposed between the first end of the sheath 48 and a first sealing element 54; and a second bellows 56 interposed between the second end of the sheath 50 and a second sealing element 58. The bellows 52, 56 and sealing elements 54, 58 are substantially identical in form and function to the sealing element 18 and bellows 24 that are described with respect to FIG. 1.

Depending on the selected application, the sheath of FIG. 5 does not need to be symmetrical. In other words, the sheath, bellows, and seal can have different diameters on each of their ends. For example, the first sheath end 48, bellows 52, and sealing element 54 can be dimensioned to comfortably seal around a wearer's calf or waist, whereas the second sheath end 50, bellows 56, and sealing element 58 can be dimensioned to comfortable around the wearer's thigh or chest. As with each of the preceding embodiments, the waterproof enclosure of FIG. 5 can include a gas passage 32 and a port 34 to permit gas removal from the enclosure.

Although the invention has been shown and described with respect to exemplary embodiments thereof, various other changes, omissions and additions in form and detail thereof may be made therein without departing from the spirit and scope of the invention.

What is claimed is:

1. A waterproof enclosure comprising:

a pliable, waterproof, elongated sheath having an open first end, an interior surface, and an exterior surface;

a resilient, waterproof, sealing element having a first end and a second end; and a first pliable, waterproof bellows having a first end and a second end, the bellows being interposed between the sheath and the sealing element, wherein the first end of the bellows is joined to the second end of the sealing element and the second end of the bellows is joined to the first end of the sheath;

wherein the sheath is continuous and the ends of the bellows are contiguous with the sealing elements and the sheath.

2. The waterproof enclosure of claim 1, wherein a second end of the sheath is open and further comprising a second resilient, waterproof sealing element having a first end and a second end; and a second pliable, waterproof bellows having a first end and a second end, the second bellows being interposed between the sheath and the second sealing element, wherein the first end of the second bellows is joined to the second end of the second sealing element and the second end of the second bellows is joined to the second end of the sheath.

3. The waterproof enclosure of claim 2, wherein the first sealing element has a greater diameter than the second sealing element.

4. The waterproof enclosure of claim 1, wherein the sealing element has a frustroconical shape, an interior face, an exterior face, and a plurality of ribs that bulge from the interior face of the sealing element.

5. The waterproof enclosure of claim 4, wherein each of the ribs extends beyond the interior face a distance in a range from 1 mm to 10 mm.

6. The waterproof enclosure of claim 5, wherein at least some of the ribs extend beyond the interior face a different distance than other ribs.

7. The waterproof enclosure of claim 4, wherein the plurality of ribs are unevenly spaced apart.

8. The waterproof enclosure of claim 4, wherein the open first end of the sheath defines a plane, wherein each of the plurality of ribs are annular and define ring planes, and wherein the ring planes are substantially parallel to the plane defined by the plane defined by the open first end of the sheath.

9. The waterproof enclosure of claim 4, wherein each of the ribs are radially disposed about the interior face of the sealing element.

10. The waterproof enclosure of claim 1, further including a port that permits gas to pass from the interior of the sheath to the exterior of the sheath when the gas pressure within the sheath exceeds a predetermined pressure.

11. The waterproof enclosure of claim 1, further including a plurality of opposing pairs of loops integral with the exterior surface of the sheath.

12. The waterproof enclosure of claim 11, further comprising a plurality of elasticized cords, each cord having a first end, a second end and an intermediate portion between the first and the second end, wherein each cord is attached to a loop and contacts the sheath at only the first end of the cord.

13. The waterproof cover of claim 1, further comprising an apertured covering that encloses at least a portion of the waterproof enclosure.

14. A waterproof enclosure comprising:

a pliable, waterproof, elongated sheath having an open first end, an interior surface, and an exterior surface;

a resilient, waterproof, sealing element having a first end and a second end, the second end of the sealing element being adjacent to the first end of the sheath;

an apertured covering that encloses at least a portion of the waterproof enclosure; and a loop integral with the exterior surface of the covering.

15. A waterproof enclosure comprising:

a pliable, waterproof, elongated sheath having a closed distal end and an open proximal end, an interior surface, and an exterior surface;

a resilient, waterproof, frustroconical, ribbed sealing element having a distal end and a proximal end, the proximal end having a smaller diameter than the distal end;

a pliable, waterproof bellows interposed between and contiguous with the distal end of the sealing element and the proximal end of the sheath;

a gas passage through the sheath, the gas passage including a pressure relief valve that actuates gas movement through the gas passage from a first state for inhibiting gas movement through the gas passage and a second state for permitting gas movement through the gas passage at a predetermined gas pressure;

an apertured covering that encloses at least a portion of the sheath;

a loop integral with the exterior surface of the covering; and an elasticized cord attached to the loop.

* * * * *